United States Patent
Lugmair et al.

(10) Patent No.: US 7,531,681 B2
(45) Date of Patent: May 12, 2009

(54) PROCESS FOR THE AMMOXIDATION OF PROPANE AND ISOBUTANE

(75) Inventors: Claus G. Lugmair, San Jose, CA (US); Steven Alan Cohen, Naperville, IL (US)

(73) Assignee: INEOS USA LLC, Lisle, IL (US)

( * ) Notice: Subject to any disclaimer, the term of this patent is extended or adjusted under 35 U.S.C. 154(b) by 264 days.

(21) Appl. No.: 11/675,838

(22) Filed: Feb. 16, 2007

(65) Prior Publication Data

US 2008/0200715 A1  Aug. 21, 2008

(51) Int. Cl.
*C07B 43/08* (2006.01)

(52) U.S. Cl. ........... 558/319; 502/312

(58) Field of Classification Search ........ None
See application file for complete search history.

(56) References Cited

U.S. PATENT DOCUMENTS

| | | | |
|---|---|---|---|
| 5,231,214 A | 7/1993 | Ushikobu et al. | 558/319 |
| 5,281,745 A | 1/1994 | Ushikobu et al. | 558/319 |
| 5,750,760 A | 5/1998 | Ushikubo | 558/319 |
| 5,907,052 A | 5/1999 | Hamada et al. | 558/320 |
| 5,973,186 A | 10/1999 | Midorikawa | 558/319 |
| 6,036,880 A | 3/2000 | Komada | 252/183.13 |
| 6,043,186 A | 3/2000 | Komada et al. | 502/312 |
| 6,063,728 A | 5/2000 | Hinago et al. | 502/300 |
| 6,080,882 A | 6/2000 | Midorikawa | 558/319 |
| 6,143,690 A | 11/2000 | Komada et al. | 502/211 |
| 6,143,916 A | 11/2000 | Hinago et al. | 558/321 |
| 6,514,902 B1 | 2/2003 | Inoue et al. | 502/305 |
| 6,610,629 B2 | 8/2003 | Hinago et al. | 502/300 |
| 2002/0115879 A1 | 8/2002 | Hinago et al. | 558/323 |
| 2003/0088118 A1 | 5/2003 | Komada et al. | 558/332 |
| 2004/0063990 A1 | 4/2004 | Gaffney et al. | 558/322 |
| 2006/0004228 A1 | 1/2006 | Hazin et al. | 562/527 |

FOREIGN PATENT DOCUMENTS

| | | |
|---|---|---|
| JP | 11/114426 | 4/1999 |
| JP | 2000/1126599 | 5/2000 |
| WO | WO2004/108278 | 12/2004 |

*Primary Examiner*—Kamal A Saeed
(74) *Attorney, Agent, or Firm*—David P. Yusko; James J. Drake; Vik Panchal

(57) ABSTRACT

A process for the ammoxidation of a saturated or unsaturated or mixture of saturated and unsaturated hydrocarbon to produce an unsaturated nitrile, said process comprising contacting the saturated or unsaturated or mixture of saturated and unsaturated hydrocarbon with ammonia and an oxygen-containing gas in the presence of a catalyst composition comprising molybdenum, vanadium, antimony, niobium, tellurium, optionally at least one element select from the group consisting of titanium, tin, germanium, zirconium, hafnium, and optionally at least one lanthanide selected from the group consisting of lanthanum, cerium, praseodymium, neodymium, samarium, europium, gadolinium, dysprosium, holmium, erbium, thulium, ytterbium and lutetium. Such catalyst compositions are effective for the gas-phase conversion of propane to acrylonitrile and isobutane to methacrylonitrile (via ammoxidation).

12 Claims, No Drawings

PROCESS FOR THE AMMOXIDATION OF PROPANE AND ISOBUTANE

BACKGROUND OF THE INVENTION

1. Field of the Invention

The present invention generally relates to a process for the ammoxidation or oxidation of a saturated or unsaturated hydrocarbon to produce an unsaturated nitrile or an unsaturated organic acid.

The invention particularly relates to a process for the gas-phase conversion of propane to acrylonitrile and isobutane to methacrylonitrile (via ammoxidation) or of propane to acrylic acid and isobutane to methacrylic acid (via oxidation).

2. Description of the Prior Art

Mixed metal oxide catalysts have been employed for the conversion of propane to acrylonitrile and isobutane to methacrylonitrile (via an ammoxidation reaction) and/or for conversion of propane to acrylic acid (via an oxidation reaction). The art known in this field includes numerous patents and patent applications, including for example, U.S. Pat. No. 5,750,760 to Ushikubo et al., U.S. Pat. No. 6,036,880 to Komada et al., U.S. Pat. No. 6,043,186 to Komada et al., U.S. Pat. No. 6,143,916 to Hinago et al., U.S. Pat. No. 6,514,902 to Inoue et al., U.S. Patent Application No. US 2003/0088118 A1 by Komada et al., U.S. Patent Application No. 2004/0063990 A1 to Gaffney et al., PCT Patent Application No. WO 2004/108278 A1 by Asahi Kasei Kabushiki Kaisha, Japanese Patent Application No. JP 1999/114426 A by Asahi Chemical Co., and Japanese Patent Application No. JP 2000/1126599 A by Asahi Chemical Co.

Although advancements have been made in the art in connection with catalysts containing molybdenum, vanadium, antimony and niobium effective for the conversion of propane to acrylonitrile and isobutane to methacrylonitrile (via an ammoxidation reaction) and/or for the conversion of propane to acrylic acid and isobutane to methacrylic acid (via an oxidation reaction), the catalysts need further improvement before becoming commercially viable. In general, the art-known catalytic systems for such reactions suffer from generally low yields of the desired product.

Tellurium can become volatile at the temperatures used for the ammoxidation of propane and isobutane and/or for the conversion of propane to acrylic acid and isobutane to methacrylic acid (via an oxidation reaction). Catalysts containing relatively high amounts of tellurium have exhibited a loss of tellurium during the ammoxidation or oxidation operation. Catalyst performance can be negatively impacted by the loss of tellurium.

SUMMARY OF THE INVENTION

In one aspect, the present invention relates to a process for the ammoxidation of a saturated or unsaturated or mixture of saturated and unsaturated hydrocarbon to produce an unsaturated nitrile, the process comprising contacting the saturated or unsaturated or mixture of saturated and unsaturated hydrocarbon with ammonia and an oxygen-containing gas in the presence of a catalyst composition comprising molybdenum, vanadium, antimony, niobium, tellurium, optionally at least one element selected from the group consisting of titanium, tin, germanium, zirconium, and hafnium, and optionally at least one lanthanide selected from the group consisting of lanthanum, cerium, praseodymium, neodymium, samarium, europium, gadolinium, dysprosium, holmium, erbium, thulium, ytterbium, and lutetium.

In one embodiment, the present invention is a process for the conversion of a hydrocarbon selected from the group consisting of propane, isobutane or mixtures thereof, to acrylonitrile, methacrylonitrile, or mixtures thereof, the process comprising the step of reacting in the vapor phase at an elevated temperature said hydrocarbon with a molecular oxygen-containing gas and ammonia, in the presence of a catalyst composition comprising molybdenum, vanadium, antimony, niobium, tellurium, optionally at least one element selected from the group consisting of titanium, tin, germanium, zirconium, and hafnium, and optionally at least one lanthanide selected from the group consisting of lanthanum, cerium, praseodymium, neodymium, samarium, europium, gadolinium, dysprosium, holmium, erbium, thulium, ytterbium, and lutetium.

In another aspect, the present invention also relates to ammoxidation catalyst compositions comprising molybdenum, vanadium, antimony, niobium, tellurium, optionally at least one element selected from the group consisting of titanium, tin, germanium, zirconium, and hafnium, and optionally at least one lanthanide selected from the group consisting of lanthanum, cerium, praseodymium, neodymium, samarium, europium, gadolinium, dysprosium, holmium, erbium, thulium, ytterbium, and lutetium.

In one embodiment, the catalyst composition comprises a mixed oxide of empirical formula:

$$Mo_1V_aSb_bNb_cTe_dX_eL_fO_n$$

wherein
X is selected from the group consisting of Ti, Sn, Ge, Zr, Hf, and mixtures thereof,
L is selected from the group consisting of La, Ce, Pr, Nd, Sm, Eu, Gd, Tb, Dy, Ho, Er, Tm, Yb, Lu and mixtures thereof,
$0.1 < a < 0.8$,
$0.01 < b < 0.6$,
$0.001 < c < 0.3$,
$0.001 < d < 0.04$,
$0 \leq e < 0.6$,
$0 \leq f < 0.1$; and
n is the number of oxygen atoms required to satisfy valance requirements of all other elements present in the mixed oxide with the proviso that one or more of the other elements in the mixed oxide can be present in an oxidation state lower than its highest oxidation state, and
a, b, c, d, e and f represent the molar ratio of the corresponding element to one mole of Mo.
In other embodiments X is Ti, Sn or mixtures thereof.
In other embodiments, L is Nd, Ce, or Pr.

DETAILED DESCRIPTION OF THE INVENTION

The present invention generally relates to a process for the (amm)oxidation of a saturated or unsaturated hydrocarbon, and catalyst compositions that may be used in the process. Such processes are effective for the ammoxidation of propane to acrylonitrile and isobutane to methacrylonitrile and/or for the conversion of propane to acrylic acid and isobutane to methacrylic acid (via an oxidation reaction).

Catalyst Composition

In one embodiment, the catalyst composition employed in the process of the present invention comprises molybdenum, vanadium, antimony, niobium, tellurium, optionally at least one element selected from the group consisting of titanium, tin, germanium, zirconium, and hafnium, and optionally at least one lanthanide selected from the group consisting of lanthanum, cerium, praseodymium, neodymium, samarium, europium, gadolinium, dysprosium, holmium, erbium, thulium, ytterbium, and lutetium. As used herein, "at least one element selected from the group . . . " or "at least one lanthanide selected from the group . . . " includes within in its scope mixtures of two or more of the listed elements or lanthanides, respectively.

In one embodiment, the catalyst composition comprises a mixed oxide of empirical formula:

$$Mo_1V_aSb_bNb_cTe_dX_eL_fO_n$$

wherein
X is selected from the group consisting of Ti, Sn, Ge, Zr, Hf, and mixtures thereof;
L is selected from the group consisting of La, Ce, Pr, Nd, Sm, Eu, Gd, Tb, Dy, Ho, Er, Tm, Yb, Lu and mixtures thereof;
$0.1<a<0.8$,
$0.01<b<0.6$,
$0.001<c<0.3$,
$0.001<d<0.04$,
$0\leq e<0.6$,
$0\leq f<0.1$; and
n is the number of oxygen atoms required to satisfy valance requirements of all other elements present in the mixed oxide with the proviso that one or more of the other elements in the mixed oxide can be present in an oxidation state lower than its highest oxidation state, and,
a, b, c, d, e and f represent the molar ratio of the corresponding element to one mole of Mo.

In one embodiment, the catalyst composition comprises a mixed oxide of empirical formula:

$$Mo_1V_aSb_bNb_cTe_dX_eL_fO_n$$

wherein
X is selected from the group consisting of Ti, Sn, and mixtures thereof;
L is selected from the group consisting of La, Ce, Pr, Nd, Sm, Eu, Gd, Tb, Dy, Ho, Er, Tm, Yb, Lu and mixtures thereof;
$0.1<a<0.8$,
$0.01<b<0.6$,
$0.001<c<0.3$,
$0.001<d<0.04$,
$0\leq e<0.6$,
$0\leq f<0.1$; and
n is the number of oxygen atoms required to satisfy valance requirements of all other elements present in the mixed oxide with the proviso that one or more of the other elements in the mixed oxide can be present in an oxidation state lower than its highest oxidation state, and
a, b, c, d, e and f represent the molar ratio of the corresponding element to one mole of Mo.

In other embodiments of the catalyst compositions described by the above empirical formulas, X is one of Ti or Sn. In other embodiments of the catalyst compositions described by the above empirical formulas, X is Ti, X is Sn, X is Ge, X is Zr, and X is Hf.

In other embodiments of the catalyst compositions described by the above empirical formulas, L is one of Nd, Ce, or Pr. In other embodiments of the catalyst compositions described by the above empirical formulas, L is La, L is Ce, L is Pr, L is Nd, L is Sm, L is Eu, L is Gd, L is Tb, L is Dy, L is Ho, L is Er, L is Tm, L is Yb, and L is Lu.

In another embodiment of the catalyst compositions described by the above empirical formulas, the catalyst composition contains no tantalum.

In other embodiments of the catalyst compositions described by the above empirical formulas, a, b, c, d, e, and f are each independently within the following ranges: $0.1<a$, $0.2<a$, $a<0.4$, $a<0.8$, $0.01<b$, $0.1<b$, $b<0.3$, $b<0.4$, $b<0.6$, $0.001<c$, $0.01<c$, $0.02<c$, $0.03<c$, $0.04<c$, $c<0.1$, $c<0.12$, $c<0.15$, $c<0.2$, $c<0.3$, $0.001<d$, $0.002<d$, $0.005<d$, $d<0.025$, $d<0.03$, $d<0.04$, $0\leq e$, $0.001<e$, $0.002<e$, $e<0.05$, $e<0.1$, $e<0.15$, $e<0.2$, $e<0.3$, $e<0.6$ and $0\leq f$, $0.001<f$, $0.002<f$, $0.003<f$, and $0.004<f$, $f<0.006$, $f<0.01$, $f<0.015$, $f<0.02$, $f<0.05$, $f<0.1$.

In one embodiment of the catalyst compositions described by the above empirical formulas, the catalyst additionally contains lithium and may optionally contain one or more other alkali metals. In this embodiment the catalyst composition comprises a mixed oxide of the empirical formula $$Mo_1V_aSb_bNb_cTe_dX_eL_fA_gLi_hO_n$$

wherein X, L, a, b, c, d, e, f, and n are previously described herein, A is at least one of Na, K, Cs, Rb and mixtures thereof, $0\leq g<0.1$, $0\leq h<0.1$, and "g" and "h" represent the molar ratio of the corresponding element to one mole of Mo. In other embodiments of the catalyst composition comprising a mixed oxide described by the above empirical formula, the catalyst composition contains no Na, K, Cs, Rb or mixtures thereof (i.e. g equals 0). In other embodiments of the catalyst composition comprising a mixed oxide described by the above empirical formula, $0<h$, $0.005<h$, $0.03<h$, $h<0.06$, $h<0.1$.

The catalyst of the present invention may be made either supported or unsupported (i.e. the catalyst may comprise a support or may be a bulk catalyst). Suitable supports are silica, alumina, zirconia, titania, or mixtures thereof. However, when zirconia or titania are used as support materials then the ratio of molybdenum to zirconium or titanium increases over the values shown in the above formulas, such that the Mo to Zr or Ti ratio is between about 1:1 to 1:10. A support typically serves as a binder for the catalyst resulting in a harder and more attrition resistant catalyst. However, for commercial applications, an appropriate blend of both the active phase (i.e. the complex of catalytic oxides described above) and the support is helpful to obtain an acceptable activity and hardness (attrition resistance) for the catalyst. Directionally, any increase in the amount of the active phase decreases the hardness of the catalyst. The support comprises between 10 and 90 weight percent of the supported catalyst. Typically, the support comprises between 40 and 60 weight percent of the supported catalyst. In one embodiment of this invention, the support may comprise as little as about 10 weight percent of the supported catalyst. In one embodiment of this invention, the support may comprise as little as about 30 weight percent of the supported catalyst. In another embodiment of this invention, the support may comprise as much as about 70 weight percent of the supported catalyst. Support materials are available which may contain one or more promoter elements, e.g. a silica sol containing sodium (Na), and such promoter elements may be incorporated into the catalyst via the support material. In one embodiment, the support comprises a low-sodium silica.

Catalyst Preparation

The catalyst compositions described herein can be prepared by hydrothermal synthesis methods. Hydrothermal synthesis methods are disclosed in U.S. Patent Application No. 2003/0004379 to Gaffney et al., Watanabe et al., "New Synthesis Route for Mo—V—Nb—Te mixed oxides catalyst for propane ammoxidation", Applied Catalysis A: General, 194-195, pp. 479-485 (2000), and Ueda et al., "Selective Oxidation of Light Alkanes over hydrothermally synthesized Mo—V-M-O (M=Al, Ga, Bi, Sb and Te) oxide catalysts", Applied Catalysis A: General, 200, pp. 135-145, which are incorporated here by reference.

In general, the catalyst compositions described herein can be prepared by hydrothermal synthesis where source compounds (i.e. compounds that contain and/or provide one or more of the metals for the mixed metal oxide catalyst composition) are admixed in an aqueous solution to form a reaction medium and reacting the reaction medium at elevated pressure and elevated temperature in a sealed reaction vessel for a time sufficient to form the mixed metal oxide. In one embodiment, the hydrothermal synthesis continues for a time sufficient to fully react any organic compounds present in the reaction medium, for example, solvents used in the preparation of the catalyst or any organic compounds added with any of the source compounds supplying the mixed metal oxide components of the catalyst composition. This embodiment simplifies further handling and processing of the mixed metal oxide catalyst.

The source compounds are reacted in the sealed reaction vessel at a temperature greater than 100° C. and at a pressure greater than ambient pressure to form a mixed metal oxide precursor. In one embodiment, the source compounds are reacted in the sealed reaction vessel at a temperature of at least about 125° C., in another embodiment at a temperature of at least about 150° C., and in yet another embodiment at a temperature of at least about 175° C. In one embodiment, the source compounds are reacted in the sealed reaction vessel at a pressure of at least about 25 psig, and in another embodiment at a pressure of at least about 50 psig, and in yet another embodiment at a pressure of at least about 100 psig. Such sealed reaction vessels may be equipped with a pressure control device to avoid over pressurizing the vessel and/or to regulate the reaction pressure.

In one or more embodiments, the source compounds are reacted by a protocol that comprises mixing the source compounds during the reaction step. The particular mixing mechanism is not critical, and can include mixing (e.g., stirring or agitating) the components during the reaction by any effective method. Such methods include, for example, agitating the contents of the reaction vessel by shaking, tumbling or oscillating the component-containing reaction vessel. Such methods also include, for example, stirring by using a stirring member located at least partially within the reaction vessel and a driving force coupled to the stirring member or to the reaction vessel to provide relative motion between the stirring member and the reaction vessel. The stirring member can be a shaft-driven and/or shaft-supported stirring member. The driving force can be directly coupled to the stirring member or can be indirectly coupled to the stirring member (e.g., via magnetic coupling). The mixing is generally sufficient to mix the components to allow for efficient reaction between components of the reaction medium to form a more homogeneous reaction medium (e.g., and resulting in a more homogeneous mixed metal oxide precursor) as compared to an unmixed reaction. This results in more efficient consumption of starting materials and in a more uniform mixed metal oxide product. Mixing the reaction medium during the reaction step also causes the mixed metal oxide product to form in solution rather than on the sides of the reaction vessel. This allows more ready recovery and separation of the mixed metal oxide product by techniques such as centrifugation, decantation, or filtration and avoids the need to recover the majority of product from the sides of the reactor vessel. More advantageously, having the mixed metal oxide form in solution allows for particle growth on all faces of the particle rather than the limited exposed faces when the growth occurs out from the reactor wall.

It is generally desirable to maintain some headspace in the reactor vessel. The amount of headspace may depend on the vessel design or the type of agitation used if the reaction mixture is stirred. Overhead stirred reaction vessels, for example, may take 50% headspace. Typically, the headspace is filled with ambient air which provides some amount of oxygen to the reaction. However, the headspace, as is known the art, may be filled with other gases to provide reactants like $O_2$ or even an inert atmosphere such as Ar or $N_2$. The amount of headspace and gas within it depends upon the desired reaction as is known in the art.

The source compounds can be reacted in the sealed reaction vessel at an initial pH of not more than about 4. Over the course of the hydrothermal synthesis, the pH of the reaction mixture may change such that the final pH of the reaction mixture may be higher or lower than the initial pH. In one or more embodiments, the source compounds are reacted in the sealed reaction vessel at a pH of not more than about 3.5. In some embodiments, the components can be reacted in the sealed reaction vessel at a pH of not more than about 3.0, of not more than about 2.5, of not more than about 2.0, of not more than about 1.5 or of not more than about 1.0, of not more than about 0.5 or of not more than about 0. In one or more embodiments, the pH ranges from about 0 to about 4, and in other embodiments, from about 0.5 to about 3.5. In some embodiments, the pH can range from about 0.7 to about 3.3, or from about 1 to about 3. The pH may be adjusted by adding acid or base to the reaction mixture.

The source compounds can be reacted in the sealed reaction vessels at the aforementioned reaction conditions (including for example, reaction temperatures, reaction pressures, pH, stirring, etc., as described above) for a period of time sufficient to form the mixed metal oxide. In one or more embodiments, the mixed metal oxide comprises a solid state solution comprising the required elements as discussed above, and in certain embodiments at least a portion thereof includes the requisite crystalline structure for active and selective propane or isobutane oxidation and/or ammoxidation catalysts, as described below. The exact period of time is not narrowly critical, and can include for example at least about six hours, at least about twelve hours, at least about eighteen hours, at least about twenty-four hours, at least about thirty hours, at least about thirty-six hours, at least about forty-two hours, at least about forty-eight hours, at least about fifty-four hours, at least about sixty hours, at least about sixty-six hours or at least about seventy-two hours. Reaction periods of time can be even more than three days, including for example at least about four days, at least about five days, at least about six days, at least about seven days, at least about two weeks or at least about three weeks or at least about one month.

Following the reaction step, further steps of the catalyst preparation methods can include work-up steps, including for example cooling the reaction medium comprising the mixed metal oxide (e.g., to about ambient temperature), separating the solid particulates comprising the mixed metal oxide from the liquid (e.g., by centrifuging and/or decanting the supernatant, or alternatively, by filtering), washing the separated solid particulates (e.g., using distilled water or deionized water), repeating the separating step and washing steps one or more times, and effecting a final separating step. In one embodiment, the work up step comprises drying the reaction medium, such as by rotary evaporation, spray drying, freeze drying etc. This eliminates the formation of a metal containing waste stream.

After the work-up steps, the washed and separated mixed metal oxide can be dried. Drying the mixed metal oxide can be effected under ambient conditions (e.g., at a temperature of about 25° C. at atmospheric pressure), and/or in an oven. In one or more embodiments, the mixed metal oxide may be dried at a temperature ranging from about 40° C. to about 150° C., and in one embodiment of about 120° C., over a drying period of about time ranging from about five to about fifteen hours, and in one embodiment of about twelve hours. Drying can be effected under a controlled or uncontrolled atmosphere, and the drying atmosphere can be an inert gas, an oxidative gas, a reducing gas or air. In one or more embodiments, the drying atmosphere includes air.

As a further preparation step, the dried mixed metal oxide can be treated to form the mixed metal oxide catalyst. Such treatments can include for example calcinations (e.g., including heat treatments under oxidizing or reducing conditions) effected under various treatment atmospheres. The work-up mixed metal oxide can be crushed or ground prior to such treatment, and/or intermittently during such pretreatment. In one or more embodiments, the dried mixed metal oxide can be optionally crushed, and then calcined to form the mixed metal oxide catalyst. The calcination may be effected in an inert atmosphere such as nitrogen. In one or more embodiments, calcination conditions include temperatures ranging from about 400° C. to about 700° C., in certain embodiments, from about 500° C. to about 650° C., and in some embodiments, the calcination can be effected at about 600° C.

The treated (e.g., calcined) mixed metal oxide can be further mechanically treated, including for example by grinding, sieving and pressing the mixed metal oxide into its final form for use in fixed bed or fluid bed reactors. As is known in the art, grinding may be accomplished by using various methods, including jar milling, bead beating, and the like. Optimal grinding conditions may be selected depending upon the sample size and catalyst composition. Examples of commercially available grinding equipment include the Mini Beadbeater 8, available from Biospec Products, and the Geno/Grinder 2000, available from Spex Certiprep. In one embodiment, an unsupported catalyst of about 2 grams may be ground in a Beadbeater for from about 2 to about 15 minutes.

In one or more embodiments, the catalyst may be shaped into its final form prior to any calcinations or other heat treatment. For example, in the preparation of a fixed bed catalyst, the catalyst precursor slurry is typically dried by heating at an elevated temperature and then shaped (e.g. extruded, pelletized, etc.) to the desired fixed bed catalyst size and configuration prior to calcination. Similarly, in the preparation of fluid bed catalysts, the catalyst precursor slurry may be spray dried to yield microspheroidal catalyst particles having particle diameters in the range from 10 to 200 microns and then calcined.

Some source compounds containing and providing the metal components used in the synthesis of the catalyst (also referred to herein as a "source" or "sources") can be provided to the reaction vessel as aqueous solutions of the metal salts. Some source compounds of the metal components can be provided to the reaction vessels as solids or as slurries comprising solid particulates dispersed in an aqueous media. Some source compounds of the metal components can be provided to the reaction vessels as solids or as slurries comprising solid particulates dispersed in non-aqueous solvents or other non-aqueous media.

Suitable source compounds for synthesis of the catalysts as described herein include the following. A suitable molybdenum source may include molybdenum(VI) oxide ($MoO_3$), ammonium heptamolybdate or molybdic acid. A suitable vanadium source may include vanadyl sulfate, ammonium metavanadate or vanadium(V) oxide. A suitable antimony source may include antimony(III) oxide, antimony(III) acetate, antimony(III) oxalate, antimony(V) oxide, antimony (III) sulfate, or antimony(III) tartrate. A suitable niobium source may include niobium oxalate, ammonium niobium oxalate, niobium oxide, niobium ethoxide or niobic acid.

A suitable tellurium source may include telluric acid, tellurium dioxide, tellurium trioxide, or an organic tellurium compound such as methyltellurol and dimethyl tellurol.

A suitable titanium source may include rutile and/or anatase titanium dioxide ($TiO_2$), e.g. Degussa P-25, titanium isopropoxide, TiO(oxalate), TiO(acetylacetonate)$_2$, or titanium alkoxide complexes, such as Tyzor 131. A suitable tin source may include tin (II) acetate. A suitable germanium source may include germanium(IV) oxide. A suitable zirconium source may include zirconyl nitrate or zirconium (IV) oxide. A suitable hafnium source may include hafnium (IV) chloride or hafnium (IV) oxide.

Suitable lanthanum sources may include lanthanum (III) chloride or lanthanum (III) oxide, and lanthanum (III) acetate hydrate. Suitable cerium sources may include cerium (III) acetate hydrate. Suitable praseodymium sources may include praseodymium (III) chloride, praseodymium (III, IV) oxide or praseodymium (III) isopropoxide, and praseodymium (III) acetate hydrate. Suitable neodymium sources may include neodymium (III) chloride, neodymium (III) oxide or neodymium (III) isopropoxide, and neodymium (III) acetate hydrate. Suitable samarium sources may include samarium (III) chloride, samarium (III) oxide or samarium (III) isopropoxide, and samarium (III) acetate hydrate. Suitable europium sources may include europium (II) chloride, europium (III) chloride or europium (III) oxide, and europium (III) acetate hydrate. Suitable gadolinium sources may include gadolinium (III) chloride or gadolinium (III) oxide, and gadolinium (III) acetate hydrate. Suitable terbium sources include terbium (III) chloride or terbium (III) oxide, and terbium (III) acetate hydrate. Suitable dysprosium sources may include dysprosium (III) chloride, dysprosium (III) oxide or dysprosium (III) isopropoxide, and dysprosium (III) acetate hydrate. Suitable holmium sources may include holmium (III) chloride, holmium (III) oxide or holmium (III) acetate hydrate. Suitable erbium sources may include erbium (III) chloride, erbium (III) oxide or erbium (III) isopropoxide, and erbium (III) acetate hydrate. Suitable thulium sources may include thulium (III) chloride or thulium (III) oxide, and thulium (III) acetate hydrate. Suitable ytterbium sources may include ytterbium (III) chloride, ytterbium (III) oxide or ytterbium (III) isopropoxide, and ytterbium (III) acetate hydrate. Suitable sources of lutetium may include lutetium (III) chloride or lutetium (III) oxide, and lutetium (III) acetate hydrate. Nitrates of the above listed metals may also be employed as source compounds.

Solvents that may be used to prepare mixed metal oxides according to the invention include, but are not limited to, water, alcohols such as methanol, ethanol, propanol, diols (e.g. ethylene glycol, propylene glycol, etc.), organic acids such as acetic acid, as well as other polar solvents known in the art. In one or more embodiments, the metal source compounds are at least partially soluble in the solvent, at least at the reaction temperature and pressure, and in certain embodiments, the metal source compounds are slightly soluble in the solvent. In one or more embodiments, water is the solvent.

Any water suitable for use in chemical synthesis may be used. The water may, but need not be, distilled and/or deionized.

The amount of aqueous solvent in the reaction medium may vary due to the solubilities of the source compounds that are combined to form the particular mixed metal oxide. The amount of aqueous solvent should at least be sufficient to yield a slurry (a mixture of solids and liquids which is able to be stirred) of the reactants. It is typical in hydrothermal synthesis of mixed metal oxides to leave an amount of headspace in the reactor vessel.

Variations on the above methods will be recognized by those skilled in the art. For example a method for preparing the catalyst described herein having the following empirical formula:

$$MoV_{0.1-0.3}Sb_{0.1-0.3}Nb_{0.03-0.15}Te_{0.01-0.03}Ti_{0.05-0.25}L_eO_n$$

in which L is La, Ce, Pr, Nd, Sm, Eu, Gd, Tb, Dy, Ho, Er, Tm, Yb, Lu and mixtures thereof, "e" is greater than zero and less than about 0.02, and "n" is determined by the oxidized states of the other elements, comprises preparing solutions or slurries of source compounds for the catalyst. In one or the first slurry, molybdenum trioxide ($MoO_3$), antimony oxide ($Sb_2O_3$), telluric acid ($Te(OH)_6$), titanium dioxide ($TiO_2$), and at least one "L" source compound are dissolved/slurried in water at the desired ratios (all ratios are relative to molybdenum metal). In another or second solution or slurry, vanadium oxysulfate ($VOSO_4$) is dissolved/slurried in water. In an alternate embodiment, vanadium oxysulfate may be added as a solid. In another or third solution or slurry, niobic acid ($Nb_2O_5 \cdot nH_2O$) is mixed with oxalic acid ($HO_2CCO_2H$). A range of oxalic acid:niobium molar ratios may be employed. In one embodiment the oxalic acid:niobium molar ratio is about 3:1. The three solutions/slurries are combined with one another, heated with mixing to 175° C. and held at this temperature for 67 hours, and then cooled to room temperature, typically by natural heat dissipation. The cooled slurry is filtered to remove the mother liquor, and the remaining solids are washed and then dried and then calcined under nitrogen at 600° C. to activate the catalyst. The calcined catalyst is pulverized, then pelletized and sized, or spray dried for testing and/or ultimate use.

Conversion of Propane and Isobutane via Ammoxidation and Oxidation Reactions

In one or more embodiments, propane is converted to acrylonitrile and/or isobutane to methacrylonitrile, by providing one or more of the aforementioned catalysts in a gas-phase flow reactor, and contacting the catalyst with propane or isobutane in the presence of oxygen (e.g. provided to the reaction zone in a feed stream comprising an oxygen-containing gas, such as and typically air) and ammonia under reaction conditions effective to form acrylonitrile or methacrylonitrile. In certain embodiments, the feed stream comprises propane or isobutane, an oxygen-containing gas such as air, and ammonia, with the following molar ratios. In one or more embodiments, the molar ratio of propane or isobutane to oxygen is from about 0.125 to about 5, in other embodiments from about 0.25 to about 4, and in yet other embodiments, from about 0.5 to about 3.5. In one or more embodiments, the molar ratio of propane or isobutane to ammonia is from about 0.3 to about 2.5, and in other embodiments, from about 0.5 to about 2.0. The feed stream can also comprise one or more additional feed components, including acrylonitrile or methacrylonitrile product (e.g., from a recycle stream or from an earlier-stage of a multi-stage reactor), and/or steam. For example, the feed stream can comprise about 5% to about 30% by weight of one or more additional feed components, relative to the total amount of the feed stream, or by mole relative to the amount of propane or isobutane in the feed stream. In one embodiment the catalyst compositions described herein are employed in the ammoxidation of propane to acrylonitrile in a once-through process, i.e., without recycle of recovered but unreacted feed materials.

Propane can also be converted to acrylic acid and isobutane to methacrylic acid by providing one or more of the aforementioned catalysts in a gas-phase flow reactor, and contacting the catalyst with propane in the presence of oxygen (e.g. provided to the reaction zone in a feedstream comprising an oxygen-containing gas, such as and typically air) under reaction conditions effective to form acrylic acid. The feed stream for this reaction preferably comprises propane and an oxygen-containing gas such as air in a molar ratio of propane or isobutane to oxygen ranging from about 0.15 to about 5, and preferably from about 0.25 to about 2. The feed stream can also comprise one or more additional feed components, including acrylic acid or methacrylic acid product (e.g., from a recycle stream or from an earlier-stage of a multi-stage reactor), and/or steam. For example, the feed steam can comprise about 5% to about 30% by weight relative to the total amount of the feed stream, or by mole relative to the amount of propane or isobutane in the feed stream.

The specific design of the gas-phase flow reactor is not narrowly critical. Hence, the gas-phase flow reactor can be a fixed-bed reactor, a fluidized-bed reactor, or another type of reactor. The reactor can be a single reactor, or can be one reactor in a multi-stage reactor system. In one or more embodiments, the reactor comprises one or more feed inlets for feeding a reactant feed stream to a reaction zone of the reactor, a reaction zone comprising the mixed metal oxide catalyst, and an outlet for discharging reaction products and unreacted reactants.

The reaction conditions are controlled to be effective for converting the propane to acrylonitrile or acrylic acid, or for converting the isobutane to methacrylonitrile or methacrylic acid. Generally, reaction conditions include a temperature ranging from about 300° C. to about 550° C., in one or more embodiments from about 325° C. to about 500° C., in some embodiments from about 350° C. to about 450° C., and in other embodiments from about 430° C. to about 520° C. The pressure of the reaction zone can be controlled to range from about 0 psig to about 200 psig, in one or more embodiments from about 0 psig to about 100 psig, and in some embodiments from about 0 psig to about 50 psig.

Generally, the flow rate of the propane or isobutane containing feed stream through the reaction zone of the gas-phase flow reactor can be controlled to provide a weight hourly space velocity (WHSV) ranging from about 0.02 to about 5, in some embodiments from about 0.05 to about 1, and in other embodiments from about 0.1 to about 0.5, in each case, for example, in grams of propane or isobutane to grams of catalyst. In one or more embodiments, advantageous catalyst performance is seen when the WHSV is at least about 0.1, in other embodiments at least about 0.15, and in yet other embodiments, at least about 0.2.

The resulting acrylonitrile and/or acrylic acid and/or methacrylonitrile and/or methacrylic acid product can be isolated, if desired, from other side-products and/or from unreacted reactants according to methods known in the art.

One or more embodiments of the present invention, when employed in the single pass (i.e. no recycle) ammoxidation of propane, are capable of producing a yield of at least about 57 percent acrylonitrile. Certain embodiments of the present invention, when employed in the single pass (i.e. no recycle) ammoxidation of propane, are capable of producing a yield of at least about 59 percent acrylonitrile. Other embodiments of the present invention, when employed in the single pass (i.e. no recycle) ammoxidation of propane, are capable of producing a yield of at least about 61 percent acrylonitrile. The effluent of the reactor may also include $CO_x$ (carbon dioxide+ carbon monoxide), hydrogen cyanide (HCN), acetonitrile or methyl cyanide ($CH_3CN$), unreacted oxygen ($O_2$), ammonia ($NH_3$), nitrogen ($N_2$), helium (He), and entrained catalyst fines.

Advantageously, the catalyst compositions of the present invention differ from tellurium-containing catalysts described in the literature in that the catalyst compositions of the present invention do not exhibit any observable tellurium loss from the active phase when prepared and tested under the conditions described hereinabove. For example, in one or more embodiments, no observable tellurium deposit is formed in the calcination vessel or the calcination furnace when the catalyst compositions of the present invention are calcined for about 2 hours under nitrogen at a temperature of about 600° C. The catalyst compositions of the present invention exhibit enhanced stability when compared to other tellurium-containing catalysts. This enhanced stability results in less degradation in catalyst performance with time on-stream, and also enables the catalyst to maintain good performance at higher space velocity.

Specific Embodiments

In order to illustrate the instant invention, mixed metal oxide catalyst were prepared and then evaluated under various reaction conditions. The compositions listed below are nominal compositions, based on the total metals added in the catalyst preparation. Since some metals may be lost or may not completely react during the catalyst preparation, the actual composition of the finished catalyst may vary slightly from the nominal compositions shown below.

EXAMPLE #1

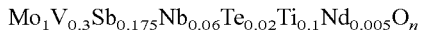
$Mo_1V_{0.3}Sb_{0.175}Nb_{0.06}Te_{0.02}Ti_{0.1}Nd_{0.005}O_n$

A 125 mL Teflon reactor liner was loaded with $MoO_3$ (8.0 g), $Sb_2O_3$ (1.418 g), $TiO_2$ (0.444 g), $Te(OH)_6$ (0.255 g), and $Nd(OAc)_3$ (2.78 mL of a 0.1 M solution) and water (10 mL). As used in this example and several subsequent examples, "$(OAc)_3$" designates the acetate hydrate for the named lanthanide metal. The mixture was stirred for about 5 minutes, after which time was introduced $VOSO_4$ (16.67 mL of a 1 M solution) and niobium oxalate (7.39 mL of a 0.451 M solution where the molar ratio of oxalate to niobium is about 3/1). Water was added to obtain an about 80% fill volume in the reactor liner. The reactor was then sealed with a Teflon cap in a metal housing, placed in an oven preheated to 175° C. and continuously rotated to effect mixing of the liquid and solid reagents. After 67 h (h=hours), the reactor was cooled and the Teflon liner was removed from the housing. The product slurry was stirred for 2 minutes, and then vacuum-filtered using a glass frit and washed by the addition of 200 mL water in three portions. The wet solid was then dried in air at 120° C. for 12 h. The resulting solid material was crushed and calcined under $N_2$ for 2 h at 600° C. The solid was then ground, pressed, and sieved to a particle size range of 145 to 355 microns and tested for catalytic performance. This material has the nominal composition $Mo_1V_{0.3}Sb_{0.175}Nb_{0.06}Te_{0.02}Ti_{0.1}Nd_{0.005}O_n$.

The material was tested as a catalyst for the heterogeneous ammoxidation of propane to acrylonitrile. At 420° C.,  WHSV=0.2 and a feed ratio of $C_3H_8/NH_3/O_2/He=1/1.2/3/12$, an acrylonitrile yield of 61% was obtained (89% propane conversion, 68% acrylonitrile selectivity).

EXAMPLE #2

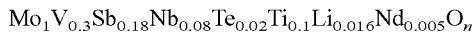
$Mo_1V_{0.3}Sb_{0.18}Nb_{0.08}Te_{0.02}Ti_{0.1}Li_{0.016}Nd_{0.005}O_n$ A first material was prepared as follows. A 23 mL Teflon reactor liner was loaded with $MoO_3$ (1.152 g), $VOSO_4$ (2.30 mL of a 1.04 M solution), niobium oxalate (1.60 mL of a 0.40 M solution where the molar ratio of oxalate to niobium is about 3/1), $Sb_2O_3$ (2.93 mL of a 0.49 M slurry), $TiO_2$ (2.85 mL of a 0.28 M slurry), Li(OAc) (1.00 mL of a 0.40 M solution), $Te(OH)_6$ (0.80 mL of a 0.20 M solution), and $Nd(OAc)_3$ (1.00 mL of a 0.04 M solution). Water was added to obtain an about 60% fill volume in the reactor liner. The reactor was then sealed with a Teflon cap in a metal housing, placed in an oven preheated to 175° C. and continuously rotated to effect mixing of the liquid and solid reagents. After 48 h the reactor was cooled and the Teflon liner was removed from the housing. The product slurry was stirred for 2 minutes, and then vacuum-filtered using a glass frit and washed three times by the addition of 150 mL water in three portions. The wet solid was then dried in air at 90° C. for 12 h. The resulting solid material was crushed and calcined under $N_2$ for 2 h at 600° C. This material has the nominal composition $Mo_1V_{0.3}Sb_{0.18}Nb_{0.08}Te_{0.02}Ti_{0.1}Li_{0.05}Nd_{0.005}O_n$.

A second material was prepared as described above for the first material, except that the lithium acetate was omitted. This second material has the nominal composition $Mo_1V_{0.3}Sb_{0.18}Nb_{0.08}Te_{0.02}Ti_{0.1}Nd_{0.005}O_n$.

A 0.45 g portion of the first material and a 0.94 g portion of the second material were combined to form a sample having the nominal composition $Mo_1V_{0.3}Sb_{0.18}Nb_{0.08}Te_{0.02}Ti_{0.1}Li_{0.016}Nd_{0.005}O_n$. The solid was then ground, pressed and sieved to a particle size range of 145 to 355 microns and tested for catalytic performance.

The material was tested as a catalyst for the heterogeneous ammoxidation of propane to acrylonitrile. At 433° C., WHSV=0.2 and a feed ratio of $C_3H_8/NH_3/O_2/N_2=1/2.0/3/12$, an acrylonitrile yield of 60% was obtained (91% propane conversion, 65% acrylonitrile selectivity).

COMPARATIVE EXAMPLE #3

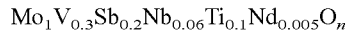
$Mo_1V_{0.3}Sb_{0.2}Nb_{0.06}Ti_{0.1}Nd_{0.005}O_n$

A 125 mL Teflon reactor liner was loaded with $MoO_3$ (8.0 g), $Sb_2O_3$ (1.620 g), $TiO_2$ (0.444 g), and $Nd(OAc)_3$ (0.0893 g) and water (10 mL). The mixture was stirred for about 5 minutes, after which time was introduced $VOSO_4$ (16.67 mL of a 1 M solution) and niobium oxalate (7.612 mL of a 0.438 M solution where the molar ratio of oxalate to niobium is about 3/1). Water was added to obtain an about 80% fill volume in the reactor liner. The reactor was then sealed with a Teflon cap in a metal housing, placed in an oven preheated to 175° C. and continuously rotated to effect mixing of the liquid and solid reagents. After 48 h, the reactor was cooled and the Teflon liner was removed from the housing. The product slurry was stirred for 2 minutes, and then vacuum-filtered using a glass frit and washed by the addition of 200 mL water in three portions. The wet solid was then dried in air at 120° C. for 12 h. The resulting solid material was crushed and calcined under $N_2$ for 2 h at 600° C. The solid was then ground, pressed, and sieved to a particle size range of 145 to 355 microns and tested for catalytic performance. This material has the nominal composition $Mo_1V_{0.3}Sb_{0.2}Nb_{0.06}Ti_{0.1}Nd_{0.005}O_n$.

The material was tested as a catalyst for the heterogeneous ammoxidation of propane to acrylonitrile. At 430° C., WHSV=0.15 and a feed ratio of $C_3H_8/NH_3/O_2/He=1/1.2/3/12$, an acrylonitrile yield of 56% was obtained (87% propane conversion, 64% acrylonitrile selectivity).

COMPARATIVE EXAMPLE #4

$Mo_1V_{0.38}Sb_{0.25}Nb_{0.075}Ti_{0.125}Nd_{0.0062}O_n$

A 200 mL Teflon reactor liner was loaded with $MoO_3$ (6.334 g), $Sb_2O_3$ (1.283 g), $TiO_2$ (0.351 g), $Nd(OAc)_3$ (0.088 g) and water (10 mL). The mixture was stirred for about 5 minutes, after which time was introduced $VOSO_4$ (13.2 mL of a 1.0 M solution) and niobium oxalate (6.083 mL of a 0.434 M solution). Water was added to obtain an about 80% fill volume of the reactor liner. The reactor was then sealed with a Teflon cap in a metal housing, placed in an oven preheated to 175° C. and continuously rotated to effect mixing of the liquid and solid reagents. After 48 h the reactor was cooled and the Teflon liner was removed from the housing. The product slurry was centrifuged to separate the solid reaction products from the liquid. The liquid was decanted and distilled water (25 mL) was added to the solid. The solid was crushed and agitated to dissolve soluble salts. The mixture was centrifuged and the liquid decanted. This washing was done twice. The wet solid was dried in air at 120° C. for 12 h. The resulting solid material was crushed and calcined under $N_2$ for 2 h at 600° C. The solid was then ground, pressed, and sieved to a particle size range of 145 to 355 microns and tested for catalytic performance. This material has the nominal composition $Mo_1V_{0.38}Sb_{0.25}Nb_{0.0075}Ti_{0.125}Nd_{0.0062}O_n$.

The material was tested as a catalyst for the heterogeneous ammoxidation of propane to acrylonitrile. At 420° C., WHSV=0.15, and feed ratio $C_3H_8/NH_3/O_2/He=1/1.2/3/12$, an acrylonitrile yield of 58% was achieved at a propane conversion of 84% and an acrylonitrile selectivity of 69%.

COMPARATIVE EXAMPLE #5

$Mo_1V_{0.3}Sb_{0.2}Nb_{0.06}Ti_{0.1}Ge_{0.05}Nd_{0.005}O_n$

A 23 mL Teflon reactor liner was loaded with $MoO_3$ (1.20 g), $Sb_2O_3$ (0.243 g), $GeO_2$ (0.0436 g) and water (2.0 mL). The mixture was stirred for about 5 minutes, after which time was introduced $VOSO_4$ (2.50 mL of a 1.0 M solution), $TiO_2$ (0.833 mL of a 0.08 g/mL slurry), $Nd(OAc)_3$ (0.417 mL of a 0.1 M solution), and niobium oxalate (1.142 mL of a 0.438M solution). Water was added to obtain an about 80% fill volume of the reactor liner. The reactor was then sealed with a Teflon cap in a metal housing, placed in an oven preheated to 175° C. and continuously rotated to effect mixing of the liquid and solid reagents. After 48 h the reactor was cooled and the Teflon liner was removed from the housing. The product slurry was centrifuged to separate the solid reaction products from the liquid. The liquid was decanted and distilled water (5 mL) was added to the solid. The solid was crushed and agitated to dissolve soluble salts. The mixture was centrifuged and the liquid decanted. This washing was done twice. The wet solid was dried in air at 120° C. for 12 h. The resulting solid material was then crushed and calcined under $N_2$ for 2 h at 600° C. The solid was then ground, pressed, and sieved to a particle size range of 145 to 355 microns and tested for catalytic performance. This material has the nominal composition $Mo_1V_{0.3}Sb_{0.2}Nb_{0.06}Ti_{0.1}Ge_{0.05}Nd_{0.005}O_n$.

The material was tested as a catalyst for the heterogeneous ammoxidation of propane to acrylonitrile. At 420° C., WHSV=0.15, and feed ratio $C_3H_8/NH_3/O_2/He=1/1.2/3/12$ an acrylonitrile yield of 58% was achieved at a propane conversion of 84% and an acrylonitrile selectivity of 69%.

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

We claim:

1. A process for the ammoxidation of a saturated or unsaturated or mixture of saturated and unsaturated hydrocarbon to produce an unsaturated nitrile, said process comprising contacting the saturated or unsaturated or mixture of saturated and unsaturated hydrocarbon with ammonia and an oxygen-containing gas in the presence of a catalyst composition comprising a mixed oxide of empirical formula:

$Mo_1V_aSb_bNb_cTe_dX_eL_fO_n$ wherein X is selected from the group consisting of Ti, Sn, Ge, Zr, Hf, and mixtures thereof; L is selected from the group consisting of La, Ce, Pr, Nd, Sm, Eu, Gd, Tb, Dy, Ho, Er, Tm, Yb, Lu and mixtures thereof;

0.1<a<0.8,
0.01<b<0.6,
0.001<c<0.3,
0.001<d<0.04,
0≦e<0.6,
0≦f<0.1; and n is the number of oxygen atoms required to satisfy valance requirements of all other elements present in the mixed oxide with the proviso that one or more of the other elements in the mixed oxide can be present in an oxidation state lower than its highest oxidation state, and wherein a, b, c, d, e and f represent the molar ratio of the corresponding element to one mole of Mo.

2. The process of claim 1, wherein in the catalyst composition: 0.2<a<0.4, 0.1<b <0.4, 0.01<c<0.2, 0.002<d<0.03, 0.001<e<0.3, and 0.001<f<0.05.

3. The process of claim 1, wherein X is selected from the group consisting of elements Ti, Sn and mixtures thereof.

4. The process of claim 1, wherein L is selected from the group consisting of elements Nd, Ce, Pr and mixtures thereof.

5. The process of claim 1, wherein the catalyst composition comprises a support selected from the group consisting of silica, alumina, zirconia, titania, or mixtures thereof.

6. The process of claim 5, wherein the support comprises about 10 to about 70 weight percent of the catalyst.

7. The process of claim 1, wherein the hydrocarbon includes propane, isobutane, or a mixture thereof.

8. The process of claim 1, wherein the process includes providing a feed stream comprising saturated or unsaturated or mixture of saturated and unsaturated hydrocarbon, ammonia, and an oxygen-containing gas, wherein the molar ratio of hydrocarbon to oxygen is from about 0.125 to about 5.

9. The process of claim 1, wherein the process includes providing a feed stream comprising saturated or unsaturated or mixture of saturated and unsaturated hydrocarbon, ammonia, and an oxygen-containing gas, wherein the molar ratio of hydrocarbon to ammonia is from about 0.3 to about 2.5.

10. The process of claim 1, wherein the process includes providing a feed stream comprising saturated or unsaturated or mixture of saturated and unsaturated hydrocarbon at a flow rate that is controlled to provide a weight hourly space velocity of at least about 0.1 grams hydrocarbon to grams of catalyst.

11. The process of claim 1, wherein the process includes providing a feed stream comprising saturated or unsaturated or mixture of saturated and unsaturated hydrocarbon at a flow rate that is controlled to provide a weight hourly space velocity of at least about 0.15 grams hydrocarbon to grams of catalyst.

12. The process of claim 1, wherein the process includes providing a feed stream comprising saturated or unsaturated or mixture of saturated and unsaturated hydrocarbon at a flow rate that is controlled to provide a weight hourly space velocity of at least about 0.2 grams hydrocarbon to grams of catalyst.

* * * * *